United States Patent [19]

Roberson

[11] Patent Number: Plant 7,409

[45] Date of Patent: Jan. 1, 1991

[54] DAYLILY CULTIVAR NAMED AZTEC YELLOW

[75] Inventor: Robert J. Roberson, The Woodlands, Tex.

[73] Assignee: American Daylily and Perennials, Grain Valley, Mo.

[21] Appl. No.: 310,290

[22] Filed: Feb. 14, 1990

[51] Int. Cl.[5] ..... A01H 5/00
[52] U.S. Cl. ..... Plt./68
[58] Field of Search ..... Plt./68

*Primary Examiner*—James R. Feyrer

*Attorney, Agent, or Firm*—Charles W. Rummler

[57] ABSTRACT

A new variety of daylily distinguished by its clear, unspotted, lemon-yellow color, and particularly characterized by its consistent ability to increase eight to twelve times per month under tissue culture laboratory propagation procedures, a character that is very uncommon for daylily propagation on a commercial scale. This new daylily cultivar has the further advantages of a very hardy growth habit when grown in the northern United States climate zones and it withstands very well the cold winter seasons.

2 Drawing Sheets

BACKGROUND OF THE INVENTION

This new variety of daylily plant originated as a seedling selected from a group of seedlings planted by me at my ranch at Houston, Tex., and resulting from my crossing of the clonal cultivar 'Aztec Gold' (unpatented) with the cultivar 'Charlime' (unpatented), my objective being to produce a plant having blooms of clear yellow color borne on a scape height of about 18 to 24 inches. A further objective was to produce such a plant that would be cold hardy throughout the northern U.S. climate zones with the ability of maintaining winter green foliage in the mild or warmer climate zones.

This new plant was selected for propagation because it most closely possessed the advantageous features that I sought and asexual reproduction of the selected plant was observed by natural dump division at Houston, Tex., with such success that propagation is now carried on in tissue culture laboratories at Houston, Tex., and on my ranch in Grain Valley, Mo., as well as at Weyhauser tissue culture labs in Apopka, Fla.

During the course of propagation of this new plant on a more-or-less commercial scale at my daylily ranches at Houston, Tex., and at Grain Valley, Mo., I have observed that the new plant is very hardy when grown in the north zone 4 and is particularly capable of withstanding the severe wintertime weather conditions. This advantage, coupled with the ability to maintain winter green foliage in the mild and warmer climate zones, provides a plant having a very wide market latitude. Furthermore, I have observed that the new plant consistently produces a clump of at least six fans per year in normal field growth and by tissue culture production may show an increase of at least ten fans or more per month.

DESCRIPTION OF THE DRAWING

My new hybrid daylily cultivar is illustrated in a first sheet by the accompanying full color printed drawing, which shows a face view of the flower of the new variety as well as some of the foliage to illustrate its character. The second sheet depicts the blooming habit in a hand rendering of one scape.

DESCRIPTION OF THE NEW PLANT

The following is a detailed description of my hybrid daylily cultivar based upon observation of plants grown at Houston, Tex. from 1981 to 1988, as well as at Grain Valley, Mo., during 1987–1988, the color designation of the flower being according to The Pantone Matching System Color Chart (PMS).

THE PLANT

Origin: Seeding.

Parentage:

*Seed parent.*—Daylily variety 'Aztec Gold' (unpatented).

*Pollen parent.*—Daylily variety 'Charlime' (unpatented).

Form: Single stem, erect and stately growing from natural clumps of the plant as grown in a garden setting.

Height: About 20 inches.

Growth rate:

*Production character.*—Six to ten fans per year.

Growth habit: Vigorous clamping rapidly with good strength.

Branching character: Moderate. Producing six to eight branches per stem.

Foliage:

*Quantity.*—Abundant, a one year clump having about 80 leaves within a stem length of about twelve to fourteen inches from the ground.

*Leaf size.*—About 1¼ inch wide and about 12 to 18 inches long.

*Leaf shape.*—Linear with entire margins and a deep longitudinal groove and occasionally undulating.

*Texture.*—Smooth.

*Aspect.*—Glossy.

*Color.*—Upper side and under side, Green.

THE BUD

Form: Generally cylindrical with obtuse tip and base.

Size at time of sepal parting: Medium.

*Diameter.*—About ⅝ inch.

*Depth.*—About 3 inches.

Opening rate: About two hours.

Length of open time: About sixteen hours.
Color: Green to yellow at opening.
Peduncle:
*Character.*—Erect and rigid.
*Color.*—Green.

THE FLOWER

Blooming habit: Recurrent, blooming profusely in early season, through midseason, and in late summer to early fall.
Size of bloom: Medium, about 4 inches in diameter and about 1¼ inches deep.
Shape: Generally flat.
Number of blooms per scape: Fifteen to twenty with one to three blooms open on any given day.
Petalage: Normal, with six imbricated segments.
*Arrangement.*—Hexagonal with two tiers of three segments each. The outer tier comprising three sepals and the inner tier comprising three petals, the bloom opening flat.
*Size.*—Outer segments (sepals): About 1⅛ inch wide and about 3 inches long. Inner segments (petals): About 1½ inch wide and about 3 inches long.
*Margin type.*—Curved and slightly ruffled.
*Texture.*—Soft.
*Appearance.*—Satiny.
*Color.*—The upper side of all petals yellow, PMS 101. The reverse side is slightly more gold.
Peduncle:
*Length.*—About ¾ inch.
*Character.*—Upright with good strength.
*Color.*—Yellow/gold.
Persistence: The flower sheds rapidly in 24 to 48 hours.

Disease resistance: This plant resists nematodes, fungal, and bacteria "root rot" as observed at Houston, Tex.
Fragrance: Very slight.
Lasting quality: On plant, about eighteen hours. As a cut flower, about twenty-four to forty-eight hours.

THE REPRODUCTIVE ORGANS

Stamens:
*Number.*—Six in arched arrangement.
*Anthers.*—Size: About 2 mm. by 4 mm. Color: Yellow, PMS 101.
Filaments:
*Length.*—About 4 cm.
*Color.*—Yellow, PMS 101.
Pollen:
*Color.*—Yellow/gold.
Pistils:
*Number.*—One.
*Style.*—Length: About 6 cm. Color: Yellow.
*Stigma.*—Color: White.
Character of ovary: Fertile; six in number; oval-bulbous shaped.

THE FRUIT

Fertility: The fruit is fertile.
Shape: Long ovoid.
Color at maturity: Green, turning brown.

I claim:

1. The new and distinct daylily, substantially as herein shown and described, particularly characterized by its vigorous clamping ability; its hardiness and ability to withstand the cold weather of the northern portions of the United States; and its ability to retain its winter green foliage in the warmer climates.

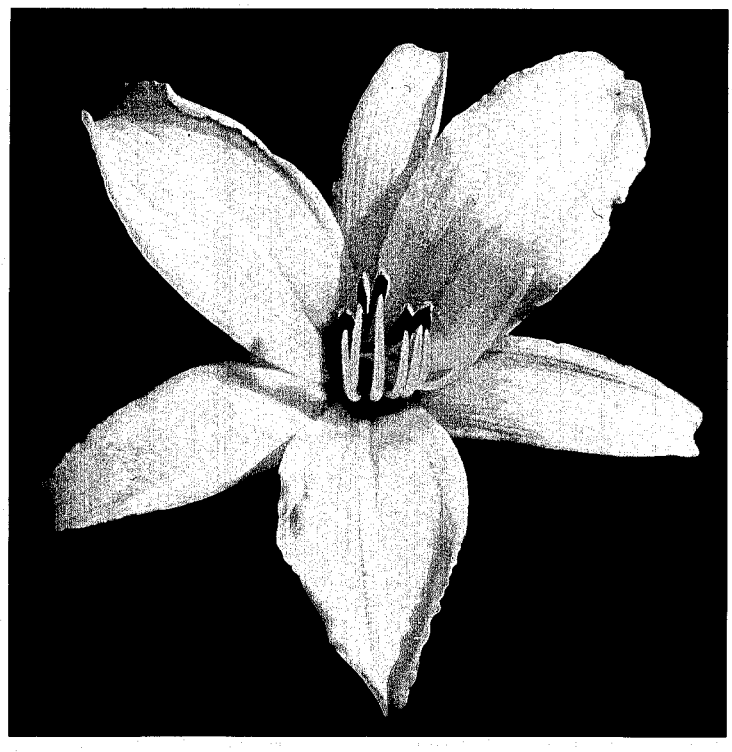

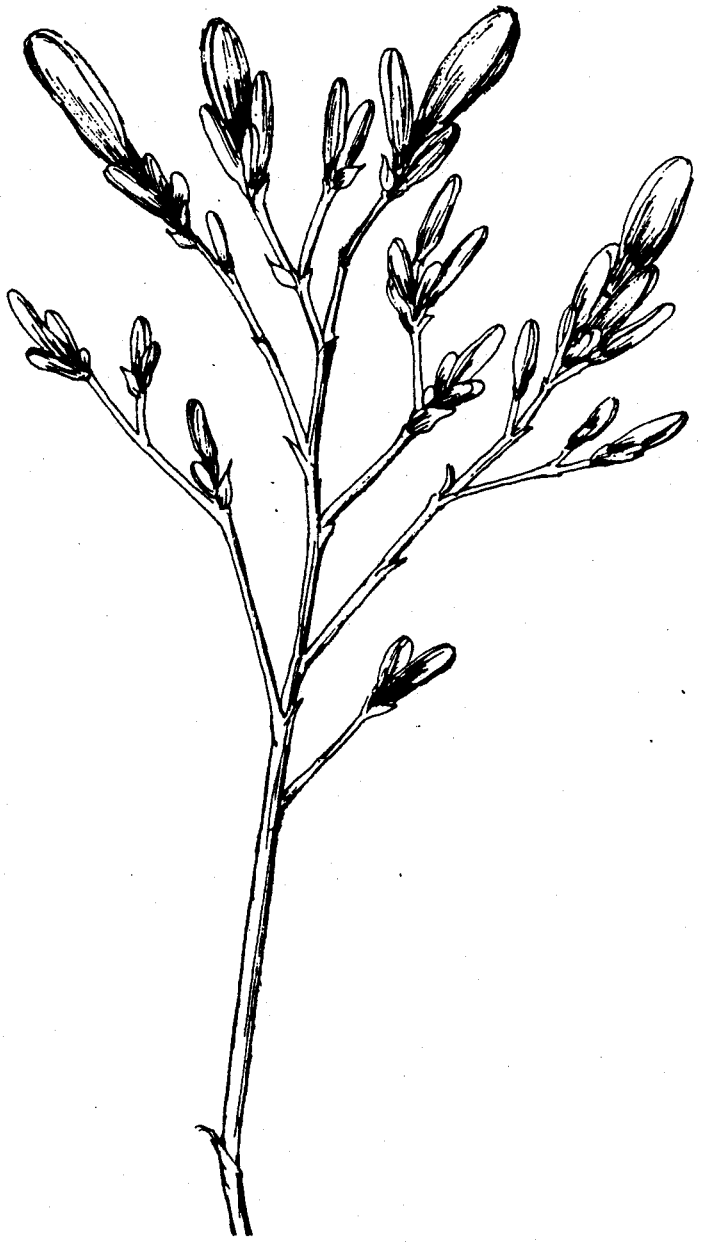

* * * * *